(12) United States Patent
Evans

(10) Patent No.: US 7,960,603 B2
(45) Date of Patent: Jun. 14, 2011

(54) MEDICAL BANDAGE COVER, MEDICAL BANDAGE, AND MEDICAL BANDAGING PRODUCT

(75) Inventor: John C. Evans, Lancashire (GB)

(73) Assignee: BSN Medical, Inc., Charlotte, NC (US)

( * ) Notice: Subject to any disclaimer, the term of this patent is extended or adjusted under 35 U.S.C. 154(b) by 84 days.

(21) Appl. No.: 12/019,672

(22) Filed: Jan. 25, 2008

(65) Prior Publication Data

US 2009/0192430 A1 Jul. 30, 2009

(51) Int. Cl.
*A61F 13/00* (2006.01)
*D04B 1/22* (2006.01)
*B32B 7/02* (2006.01)

(52) U.S. Cl. .............. 602/44; 602/8; 602/76; 66/170; 66/193; 428/216

(58) Field of Classification Search .............. 602/44, 602/8, 76; 66/170, 193; 428/216
See application file for complete search history.

(56) References Cited

U.S. PATENT DOCUMENTS

| 4,100,770 | A | | 7/1978 | Titone | |
|---|---|---|---|---|---|
| 4,235,228 | A | * | 11/1980 | Gaylord et al. | 602/8 |
| 4,807,303 | A | * | 2/1989 | Mann et al. | 2/69 |
| 5,003,970 | A | * | 4/1991 | Parker et al. | 602/50 |
| 5,382,466 | A | | 1/1995 | Ingham | |
| 5,454,780 | A | * | 10/1995 | Duback et al. | 602/8 |
| 5,461,885 | A | | 10/1995 | Yokoyama et al. | |
| 6,042,557 | A | * | 3/2000 | Ferguson et al. | 602/6 |
| 6,126,622 | A | * | 10/2000 | Darcey et al. | 602/5 |
| 7,318,812 | B2 | * | 1/2008 | Taylor et al. | 602/21 |
| 2007/0093162 | A1 | * | 4/2007 | Holcombe et al. | 442/208 |
| 2007/0276302 | A1 | | 11/2007 | Evans et al. | |
| 2009/0036812 | A1 | * | 2/2009 | Chabba et al. | 602/8 |

* cited by examiner

*Primary Examiner* — Patricia M Bianco
*Assistant Examiner* — Keri J Nelson
(74) *Attorney, Agent, or Firm* — Oliff & Berridge, PLC

(57) ABSTRACT

A medical bandage is disclosed including a knitted spacer fabric cover or padding positioned in surrounding relation on a moisture-hardenable substrate. A reactive system is applied to and into the thickness of the substrate. The reactive system having a first state wherein the substrate remains in a flexible, conformable condition and a second state wherein the reactive system hardens, simultaneously hardening the substrate into a desired conformation.

12 Claims, 18 Drawing Sheets

Guide Bar Position:      Guide Bar 3
Pattern:      0-1 / 1-0 / 0-1 / 1-0

Back Needle Bed Knitting

Front Needle Bed Knitting

Back Needle Bed Knitting

Front Needle Bed Knitting

Back Needle Bed Knitting

Front Needle Bed Knitting

Back Needle Bed Knitting

Front Needle Bed Knitting

Yarn:      Monofilament Polypropylene, 0.1mm Diameter

Fig. 20

MEDICAL BANDAGE COVER, MEDICAL BANDAGE, AND MEDICAL BANDAGING PRODUCT

TECHNICAL FIELD AND BACKGROUND OF THE INVENTION

The present invention relates generally to the field of orthopedic medicine and more specifically to the design of an improved medical bandage cover or padding, a medical bandage formed of a moisture-curable material, particularly a splint, and a medical bandaging product, each having an improved cover or padding as disclosed in this application.

Medical bandages for use in the treatment of injuries, such as broken bones requiring immobilization of a body member, historically have been formed from a strip of fabric or scrim material impregnated with a substance which hardens into a rigid structure after the strip has been wrapped around the body member. The hardening substance traditionally used in carrying out this procedure is plaster-of-paris, and much plaster-of-paris splint material is still sold throughout the world, including by the present applicant.

The above-described application procedure can be messy and time-consuming. Several components are required and considerable skill is necessary. The hardened material is subject to deterioration during wear, and can cause odor and itching. For these reasons, two or more splints or casts may be required during a single injury recovery period.

In order to alleviate the above-recited disadvantages of the conventional application procedure for plaster-of-paris casts and splints, unitary splinting materials have been devised and are disclosed in, for example, U.S. Pat. Nos. 3,900,024, 3,923,049, and 4,235,228. All of these patents describe a splint material substrate with a plurality of layers of plaster-of-paris impregnated cloth. Such unitary splinting materials are not as messy and can be applied more quickly, but still suffer from a number of disadvantages inherent in plaster-of-paris cast materials. All plaster-of-paris splints have a relatively low strength to weight ratio that results in a finished splint that is heavy and bulky. Plaster-of-paris splints are slow to harden, requiring 24 to 72 hours to reach maximum strength. Since plaster-of-paris breaks down in water, bathing and showering are difficult.

An advance in the art of casting and splinting is disclosed in U.S. Pat. Nos. 4,411,262 and 4,502,479. The casting materials disclosed in these patents comprise a flexible fabric impregnated with a moisture-curable resin enclosed in a moisture-free, moisture-impervious package. Compared to plaster-of-paris, these products are lightweight, have a very high strength to weight ratio and can be made relatively porous, permitting a flow of at least some air through the splinting material to the skin. Early prior art moisture-curing systems included a package within which was contained a "pre-cut" bandage having a plurality of layers of fabric, such as fiberglass, impregnated with the moisture-curing resin. No provision is made in these "pre-cut" bandages for re-closing the package, so that the entire material must be very quickly used after removal from the package since such moisture-curing resins will cure in a relatively short period of time due to contact even with only atmospheric moisture. In many cases, substantial wastage is created when the desired size or shape is not in inventory, and larger sizes are cut down to the required size and shape, and the remaining material discarded.

Further significant developments in the splinting area are disclosed in U.S. Pat. Nos. 4,770,299; 4,869,046; 4899738 and 5,003,970, owned by present applicant. Each of these patents discloses various roll-form, moisture-curable splint products that permit predetermined lengths of a medical bandage to be severed from a roll for use, while the remaining medical bandage is maintained in a soft, moisture-proof condition until ready for later use. These applications disclose the use of multiple layers of fiberglass fabric positioned in a synthetic, non-woven fabric protective layer, in other words, a outer cover, for residing between the hardened substrate and the patient.

The present invention relates more particularly to the cover that encloses the hardened splint substrate. The cover as disclosed in this application is a water-resistant, breathable fabric cover, and the preferred fabric is a knitted spacer fabric. The term "cover" is used in this application to include materials that are sufficiently thick to provide a padded or cushioning type of protection, as well as thinner materials that offer separation between the wearer's skin and the hardened substrate, without necessarily being thick enough to be characterized as "padding" or "cushioning material." The cover is applied to the surface of the hardened splint material on at least the side to be placed next to the skin in order to offer protection to the skin of the patient.

The knitted orthopedic cover according to the invention disclosed in this application is water resistant and therefore allows the patient to bathe, shower or swim without the concerns of getting the splint wet. The water-resistant cover is constructed in such a way as to allow maximum air movement around the injury site, making the splint more comfortable to wear. The skin of the patent is kept in a cool, low moisture environment that promotes healing while helping to prevent skin irritation and itching.

Current splint padding materials are usually constructed of non-woven synthetic fibers that are typically very dense in structure and therefore difficult to dry because of poor breathability and porosity.

Splints are often required to reside against the surface of the skin for long periods of time and can thus cause problems such as maceration of the skin. The high fiber density of known paddings and covers also keeps moisture trapped in the material which can cause bacteria to multiply to an undesirable degree.

The non-woven orthopedic padding currently used in the medical field will, when in contact with the skin of the patient, absorb into its fibrous structure perspiration and other body fluids even though the fibers themselves are hydrophobic. This absorption causes the non-woven splint padding to reduce in thickness and compact into an even denser structure. This compaction and reduction in thickness has a detrimental effect on the comfort of the padding when in contact with the skin of the patient.

To overcome these and other problems associated with the use of orthopedic non-woven splint padding, this application discloses and claims a water-resistant orthopedic splint cover material. The preferred embodiment of this water-resistant orthopedic splint cover is based on a knitted spacer fabric using a combination of monofilament and multifilament yarns.

The invention described in this application thus provides a orthopedic splint cover or padding material that is optimized for use with moisture-curing synthetic splints, and enhances the advantages provided by this type of splinting system. One such unitary system uses a knitted spacer padding placed around and encircling a substrate having moisture-curing resin applied thereto, together with a moisture-impervious package with means for resealing the package against entry of moisture after a desired length of bandaging product has been removed for use.

Another preferred embodiment of the cover and padding according to the invention permits the provision of pre-cut lengths of splint sealed against moisture intrusion until use.

SUMMARY OF THE INVENTION

It is therefore an object of the invention to provide a medical bandage cover with improved use characteristics.

It is another object of the invention to provide a medical bandage cover that has improved water and air flow characteristics.

It is another object of the invention to provide a medical bandage cover that is lightweight.

It is another object of the invention to provide a medical bandage cover that is resistant to crushing and matting during use.

It is another object of the invention to provide a medical bandage cover that has a high volume to weight ratio.

It is another object of the invention to provide a medical bandage product in roll form that includes a medical bandage cover with improved use characteristics.

It is another object of the invention to provide a medical bandaging product with a knitted cover that can be dispensed in any desired length while preventing hardening of the remaining material until use is desired.

It is another object of the invention to provide a medical bandage product in pre-cut lengths with a moisture-curable resin which hardens the material upon exposure to moisture to form a rigid, self-supporting structure.

It is another object of the invention to provide a medical bandage product that includes a protective outer padding or cover that is formed of a knitted open structure having enhanced moisture and air flow characteristics.

It is another object of the invention to provide a unitary medical bandaging product which includes a soft, protective wrapping to provide a cushion against the skin of a patient.

It is another object of the invention to provide a medical bandage product that includes a moisture-impervious enclosure in which is packaged in moisture-free conditions a medical bandage that includes a soft, protective outer wrapping, such as a padding or cover, that encloses a moisture-curable substrate of various materials and structures.

These and other objects of the present invention are achieved in the preferred embodiments disclosed below by providing a cover fabric for a medical bandage, comprising a knitted spacer fabric positioned in surrounding relation on a moisture-hardenable substrate.

According to one embodiment of the invention, the knitted spacer fabric comprises monofilament and multifilament yarns.

According to yet another embodiment of the invention, the knitted spacer fabric includes monofilament yarns that are selected from the group consisting of polyester, polypropylene, polyethylene or nylon, and multifilament yarns that are selected from the group consisting of polyester, polypropylene or nylon. The fabric thickness is between about 1 and about 10 mm and the fabric weight is between about 90 and about 200 grams/m$^2$.

According to yet another embodiment of the invention, the number of yarn filaments is between 1 and 96, and the yarn thicknesses are between 0.03 and 1.1 mm.

According to yet another embodiment of the invention, the fabric includes polypropylene yarns containing between 24 and 48 filaments, monofilament polyester yarns between 0.07 and 1.14 mm in diameter.

According to yet another embodiment of the invention, the fabric thickness is between about 1 mm and about 10 mm.

According to yet another embodiment of the invention, the fabric has a weight of about between 90 and 200 grams/m$^2$.

According to yet another embodiment of the invention, the cover fabric has a stitch pattern according to:

| | | |
|---|---|---|
| Bar1. 16-16/8-8/0-0/8-8 | Inlay over 4 needles | 18 gauge |
| Bar2. 0-4/4-4/4-0/0-0 | Chain Stitch | 18 gauge |
| Bar3. 4-8/12-8/4-8/4-0 | 3 Needle 'V' | 9 gauge |
| Bar4. 0-4/12-8/16-20/12-8 | 5 Needle 'V' | 9 gauge |
| Bar5. 4-4/4-0/0-0/0-4 | Chain stitch | 9 gauge |
| Bar6. 0-0/12-12/24-24/24-24/24/24/12-12/0-0/0-0/0-0 | Inlay over 3 needles | 9 gauge. |

All bars are fully threaded.

According to yet another embodiment of the invention, the fabric has a weight of about 160 grams/m$^2$, or about 50% of the weight of the current nonwoven padding.

According to yet another embodiment of the invention, a medical bandage is provided, comprising a protective, knitted spacer fabric cover positioned in surrounding relation on a moisture-hardenable substrate. The substrate is comprised of an elongate fabric having two opposed major faces connected by yarns extending between the faces, and two opposed, longitudinally-extending side edges defining a predetermined fabric thickness.

A reactive system is applied to and into the thickness of the substrate, the reactive system having a first state wherein the substrate remains in a flexible, conformable condition and a second state wherein the reactive system hardens, simultaneously hardening the substrate into a desired conformation.

According to yet another embodiment of the invention, the reactive system comprises a moisture-curable resin.

According to yet another embodiment of the invention, the cover fabric thickness is between about 1 mm and about 10 mm and the fabric weight is about between 90 and 200 grams/m$^2$.

According to yet another embodiment of the invention, the cover comprises a soft, flexible protective padding covering at least one of the major faces of the substrate and adapted to pass water therethrough and onto the substrate.

According to yet another embodiment of the invention, the bandage is packaged in a moisture-proof condition in a precut length suitable for a particular medical use.

According to yet another embodiment of the invention, the bandage is in the form of a roll from which desired lengths may be cut as needed.

According to yet another embodiment of the invention, a medical bandaging product is provided, comprising a sleeve formed of moisture-impervious material and sealable to prevent entry of moisture, and a medical material positioned in the sleeve and sealed therein against entry of moisture until use. The medical material comprises a substrate formed of an elongate fabric having two opposed major faces and two opposed, longitudinally-extending side edges defining a predetermined fabric thickness. A reactive system is impregnated into or coated onto the substrate. The system remains stable when maintained in substantially moisture-free conditions and hardens upon exposure to sufficient moisture to form a rigid, self supporting structure. A soft, flexible, protective knitted spacer fabric cover is positioned over at least one of the major faces of the substrate along its length to provide a barrier between the substrate and the skin of a patient when the material is in use.

According to yet another embodiment of the invention, the cover is positioned over both major faces of the substrate.

According to yet another embodiment of the invention, the cover is wrapped around and encloses both major faces and the longitudinally extending side edges of the substrate.

BRIEF DESCRIPTION OF THE DRAWINGS

Some of the objects of the invention have been set forth above. Other objects and advantages of the invention will appear as the description of the invention proceeds when taken in conjunction with the following drawings, in which:

FIGS. 18-22 illustrate a knitting pattern in accordance with an embodiment of the present invention.

DESCRIPTION OF THE PREFERRED EMBODIMENTS AND BEST MODE

Figure 1:
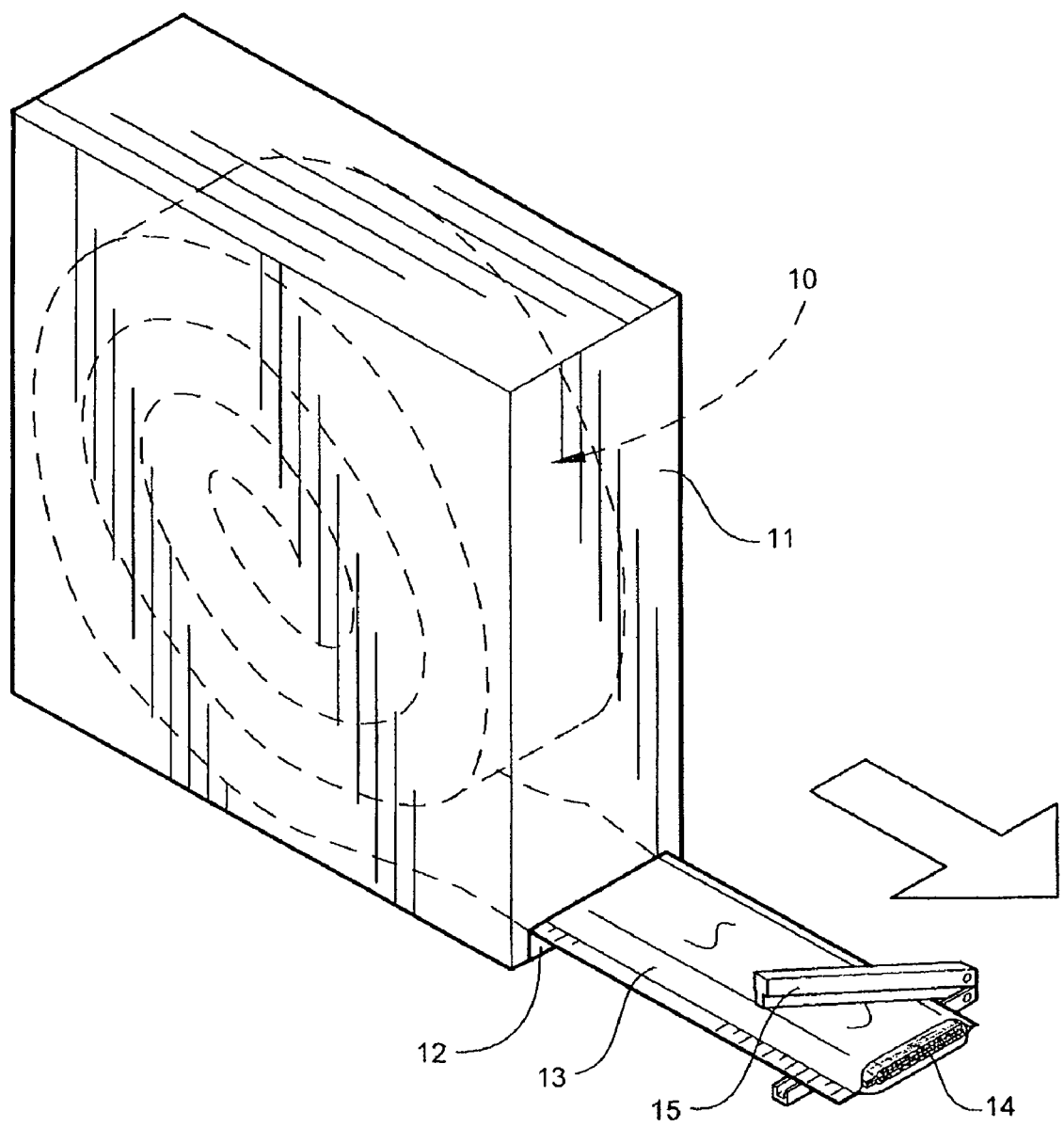
FIG. 1 is a perspective view showing a medical bandaging product according to one preferred embodiment of the invention being dispensed from a dispenser.

Referring now specifically to the drawings, a medical bandaging product according to the present invention is shown generally in FIG. 1 at 10. Bandaging product 10 may be sold in any convenient length, such as 24 feet, and is rolled into a coil and positioned in a suitable dispenser 11. Dispenser carton 11 is provided with a slot 12 at one lower corner through which bandaging product 10 is dispensed.

According to one embodiment of the invention, the bandaging product 10 is formed of an outer elongate sleeve 13 formed of a moisture-impervious material, for example, a laminated metal foil and plastic. Sleeve 13 is heat sealed along opposite, parallel extending sides to form an elongate tube. An elongate medical bandage 14, described in detail below, is positioned within sleeve 13 and is maintained in substantially moisture-free conditions until dispensed. The medical bandage 14 is dispensed by pulling the needed amount of material, along with the sleeve 13 in which it is enclosed, out of the carton 11 and severing it with, for example, scissors. The remaining, raw end of the bandage 14 is tucked back into the remaining sleeve 13 with a sufficient length of sleeve available to receive a clip, such as a bar clip 15. Of course, any suitable form of closure may be used so long as a seal is formed that is sufficient to prevent moisture intrusion.

Figure 2:
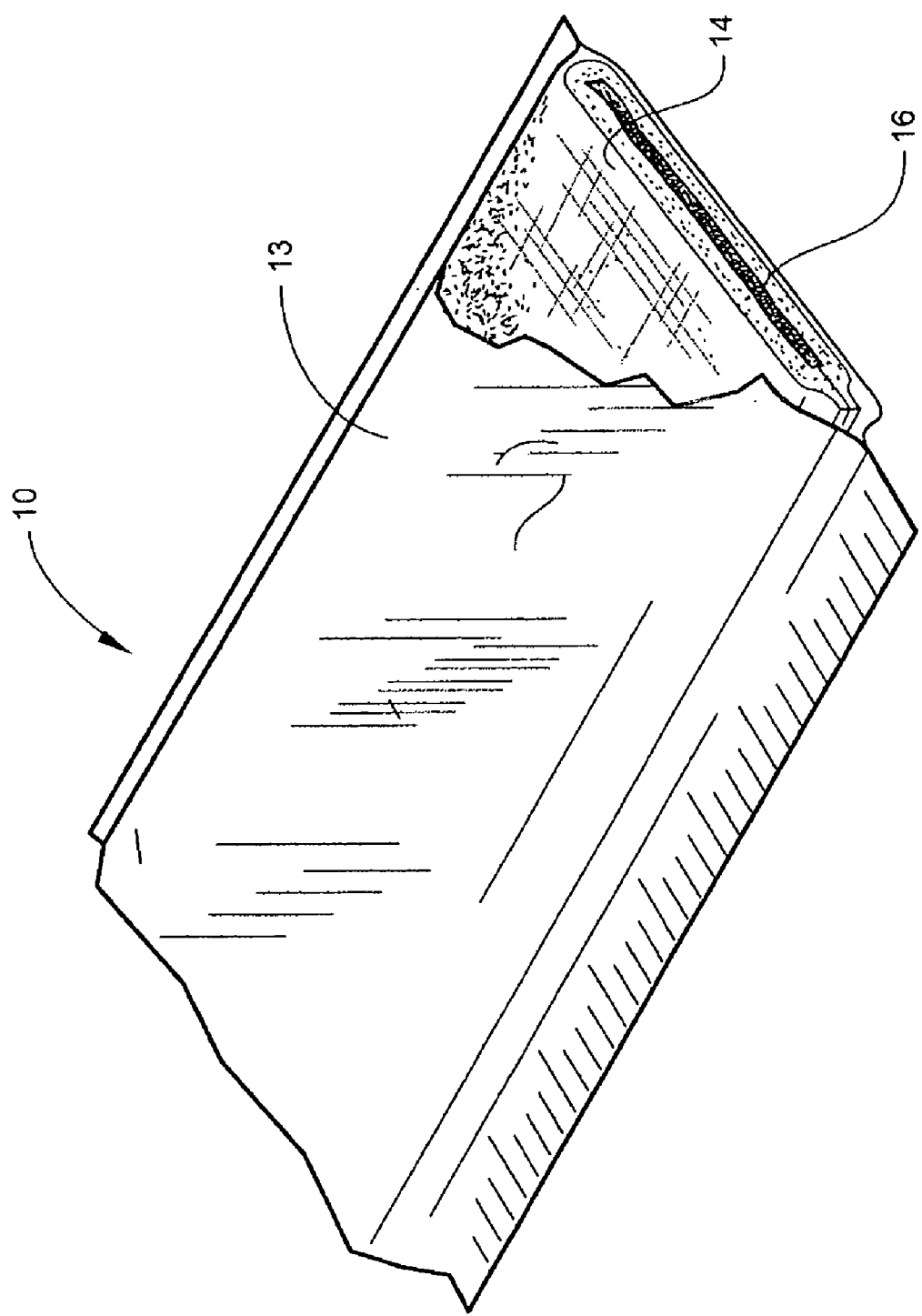
FIG. 2 is a perspective view with parts broken away of a cut length of the medical bandage product as dispensed from the dispenser.

Referring now to FIG. 2, since the appropriate length of bandage 14 is best determined by measurement, measurement marks "M" are printed on one edge of the sleeve 13. The sleeve 13 is preferably closely conforming to the bandage 14 along its length in order to reduce the amount of air that is introduced into the sleeve while it is open.

Figure 3:
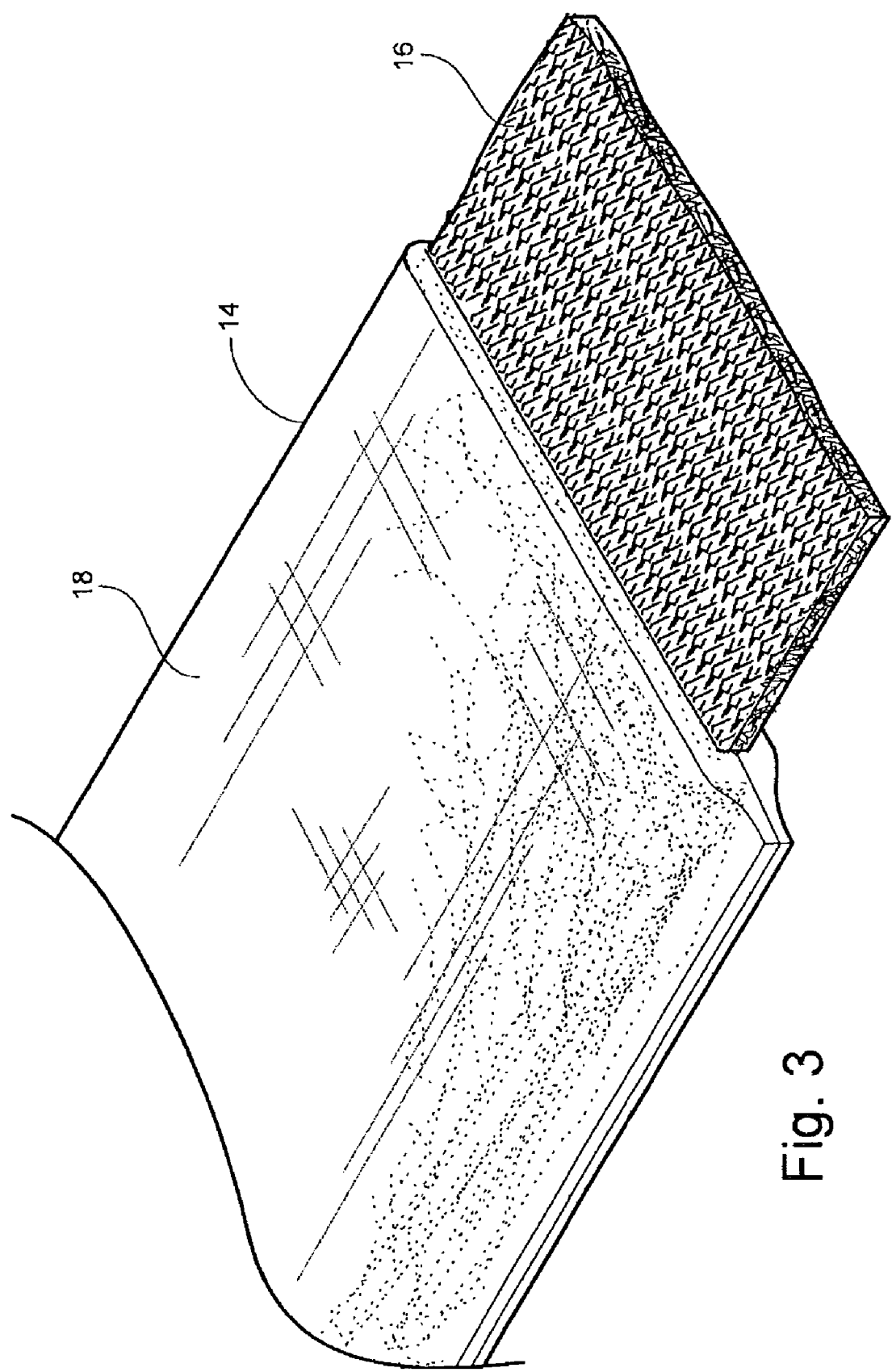
FIG. 3 is a perspective view of a length of medical bandage with a part of the outer cover removed for clarity.
Figure 4:
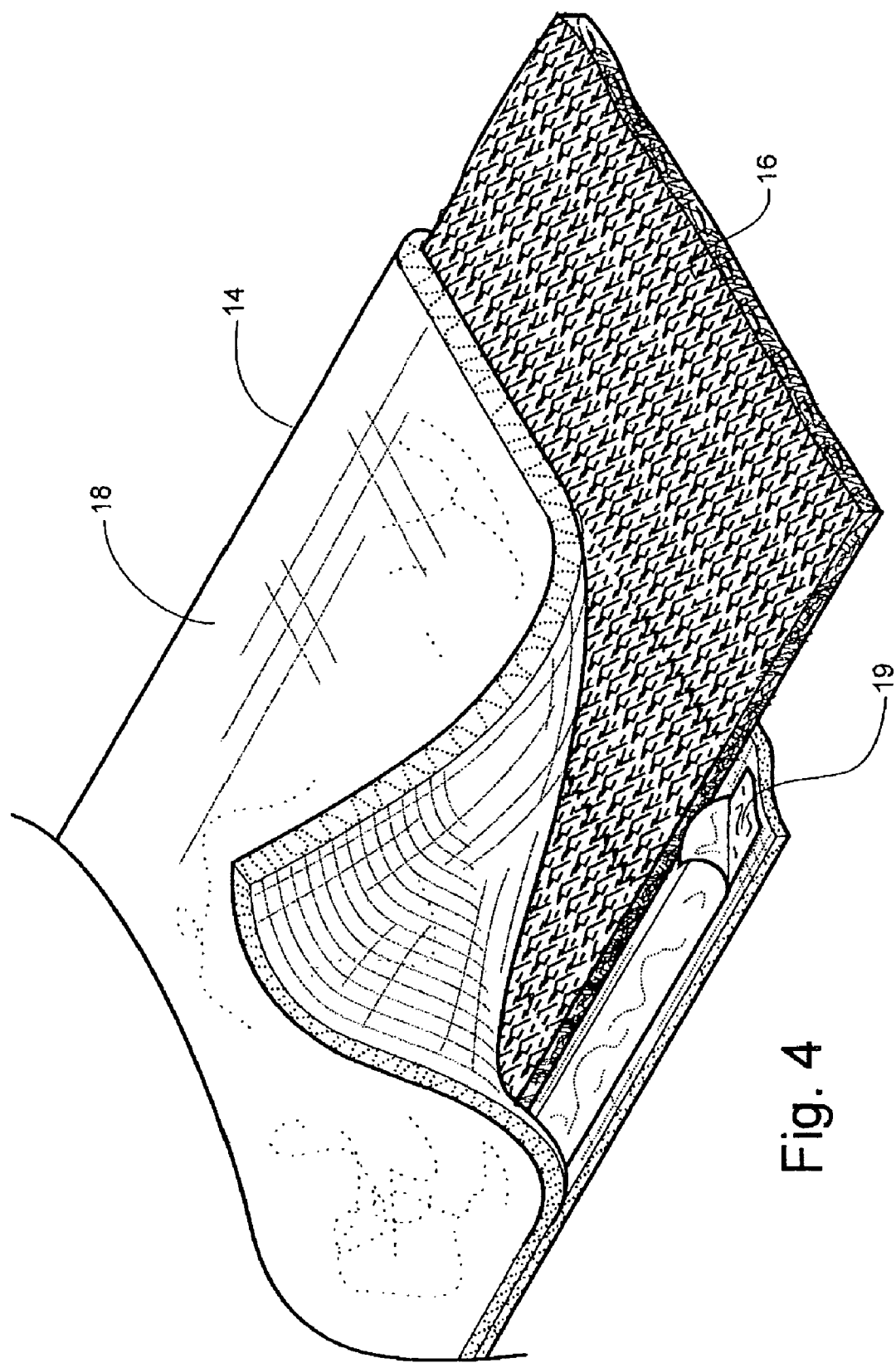
FIG. 4 is a perspective view of a length of the medical material with a non-tubular form of the cover shown, with one preferred embodiment of forming the cover around the substrate being shown.

Referring now to FIGS. 3 and 4, bandage 14 includes a substrate 16, preferably formed of a fibrous material, which may be single or multiple layers of woven, knitted fabric, or a material formed according to other processes. Examples of a suitable substrate 16 include several layers of overlaid woven fiberglass fabric and a single layer knitted fabric formed of synthetic fibers.

According to one embodiment of the invention, the substrate 16 is contained within a cover 18 that is preferably formed of a soft, flexible synthetic knitted fabric, as described in further detail below. The cover 18 provides a protective layer between the skin of the patient and substrate 16. The cover 18 may be of varying thickness, and may or may not be thick enough to be considered as having a padding or cushioning function.

The cover 18 may, as shown in FIGS. 3 and 4, be initially knitted as a flat fabric and folded around the substrate 16 to form a tubular enclosure, in which case the cover may be secured around the substrate by, for example, double-sided tape or a pressure sensitive adhesive strip 19, as shown in FIG. 4. In accordance with another preferred embodiment, the cover 18 may be knitted as a tube and pulled over the substrate 16 during manufacture.

In accordance with yet another embodiment of the invention, the substrate 16 may be packed in the sleeve 13 and enclosed within cover 18 just before application. This may be accomplished by folding a length of the cover 18 around the substrate 16 and securing it in place with tape or adhesive, as described above.

Figure 5:
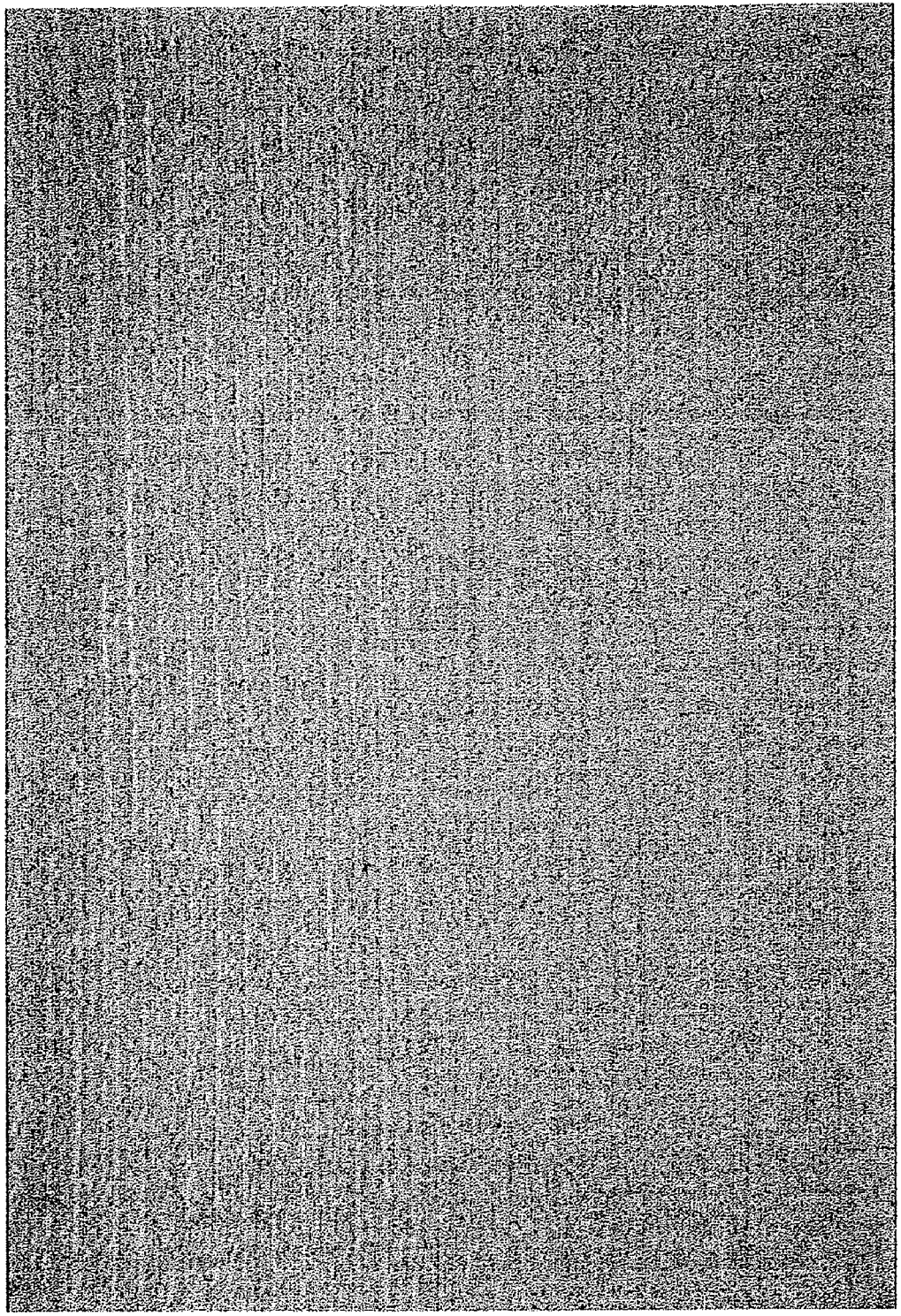
FIG. 5 is a photographic perspective view of a padding embodiment of the cover.
Figure 6:
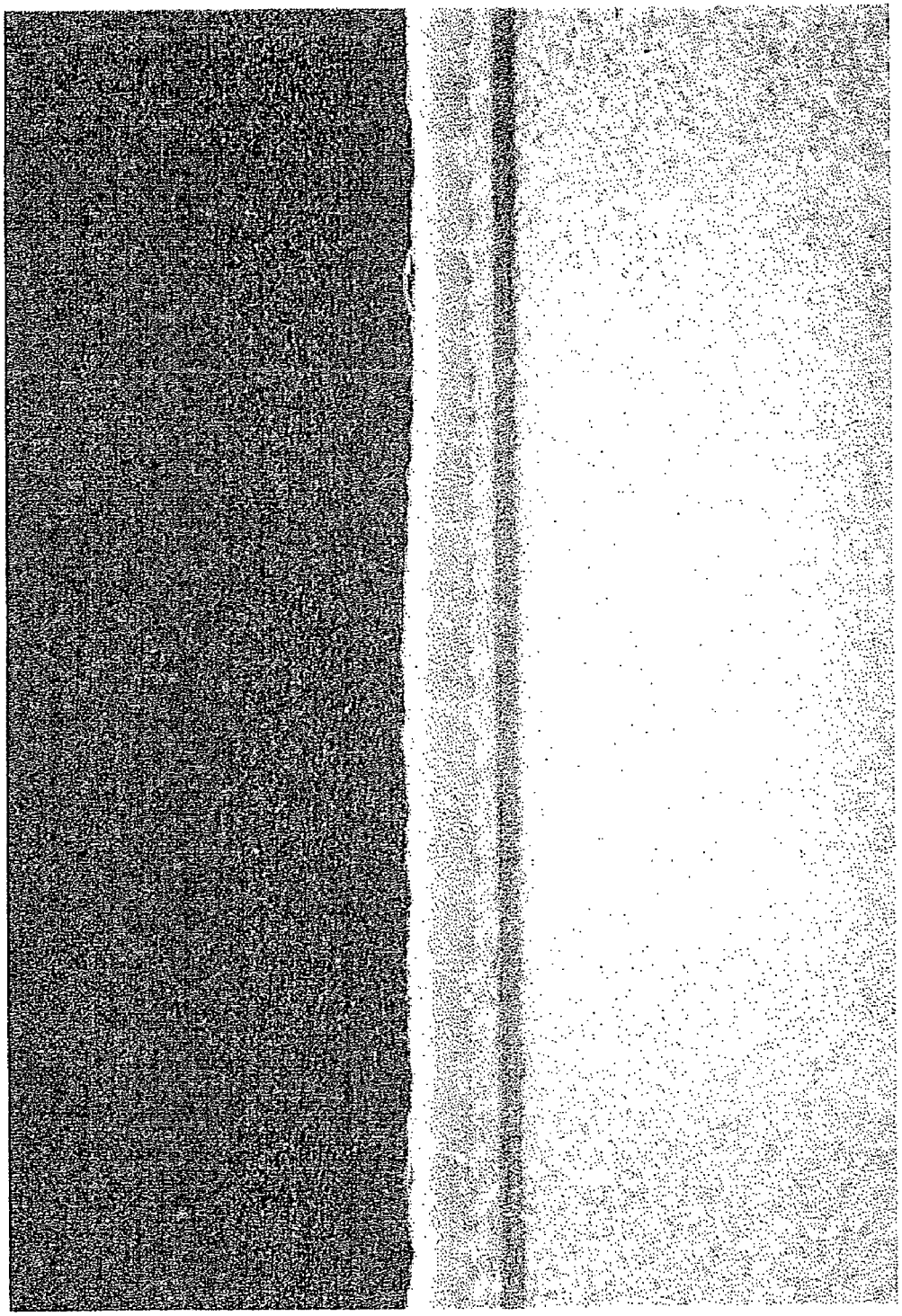
FIG. 6 is a photographic end view of a padding embodiment of the cover.

The cover 18 according to an actual physical embodiment is illustrated in FIGS. 5 and 6.

To overcome the problems associated with the use of prior orthopedic non-woven splint paddings and covers, a knitted, water-resistant, orthopedic splint cover is provided, and is based on a knitted spacer fabric using a combination of textured or flat monofilament and multifilament yarns, for example, monofilament yarns that are polyester, polypropylene, polyethylene or nylon, and multifilament yarns that are polyester, polypropylene or nylon. One construction of the knitted water-resistant orthopedic splint cover 18 uses yarns in a decitex range of 30 to 167. The number of filaments may be between 1 and 96, between 0.03 and 1.1 mm thick, and the fabric has a weight of between 90 and 200 grams/m$^2$.

In accordance with a preferred embodiment of the invention, the wales, or threads per cm are between 12 and 24 and the courses per cm are between 5 and 40 per cm. More particularly, the water-resistant orthopedic splint cover 18 is constructed from polyester monofilament yarns and polypropylene multifilament yarns. The multifilament polypropylene yarn may preferably contain between 24 and 48 filaments, and the monofilament polyester yarn may preferably be between 0.07 and 1.14 mm in diameter.

Silver nitrate may be added into the yarns to prevent the growth of bacteria.

One preferred knitting pattern for the present invention is detailed as follows:

EXAMPLE

An example according to a preferred embodiment is set out below:

Yarns:
Polypropylene 165 d/tex 48 filament; and
Polyester 0.14 mm 75 Dtex Monofilament.
Construction—18 gauge, 600 courses per meter.
The notation is:

| Bar 1. | 4 Needle Inlay | 18 gauge. | 0.14 Polyester | 16-16/8-8/0-0/8-8 |
|---|---|---|---|---|
| Bar 2. | Chain Stitch | 18 gauge | 165/48 Polpropylene | 0-4/4-4/4-0/0-0 |
| Bar 3. | 3 Needle 'V' | 9 gauge | 0.14 Polyester | 4-8/12-8/4-8/4-0 |
| Bar 4. | 5 Needle 'v' | 9 gauge | 0.14 Polyester | 0-4/12-8/16-20/12-8 |
| Bar 5. | Chain Stitch | 9 gauge | 0.14 Polyester | 0-4/12-8/16-20/12-8 |
| Bar 6. | 3 Needle Inlay | 9 gauge | 0.14 Polyester | — |
| | | | | 0-0/12-12/24-24/24-24/12-12/0-0/0-0/0-0 |

The above described stitch pattern is illustrated in FIGS. 18-22.

The weight of the knitted cover in the Example is 160 grams/m$^2$., or about 50% of the weight of the current nonwoven padding conventionally used on applicant's ORTHO-GLASS® splint product. The air permeability is significantly higher on the knitted cover that supports more healthy skin during treatment, more comfort and less complications. The nominal uncompressed thickness of the cover is 2.5 mm. The cover at this thickness can be characterized as "padding" or "cushioning."

Moisture vapor transmission rate (MVTR) ranges are 900 g/24 hrs/m$^2$ to 1050 g/24 hrs/m$^2$; more preferably 950 g/24 hrs/m$^2$. Air permeability ranges are 3200 cm$^3$/cc$^2$ per hour at 20 cm Mercury to 4500 cm$^3$/cc$^2$ per hour at 20 cm Mercury; more preferably 3400 cm$^3$/cc$^2$ hour at 20 cm Mercury, as tested to ASTM D737-96.

Figure 7:
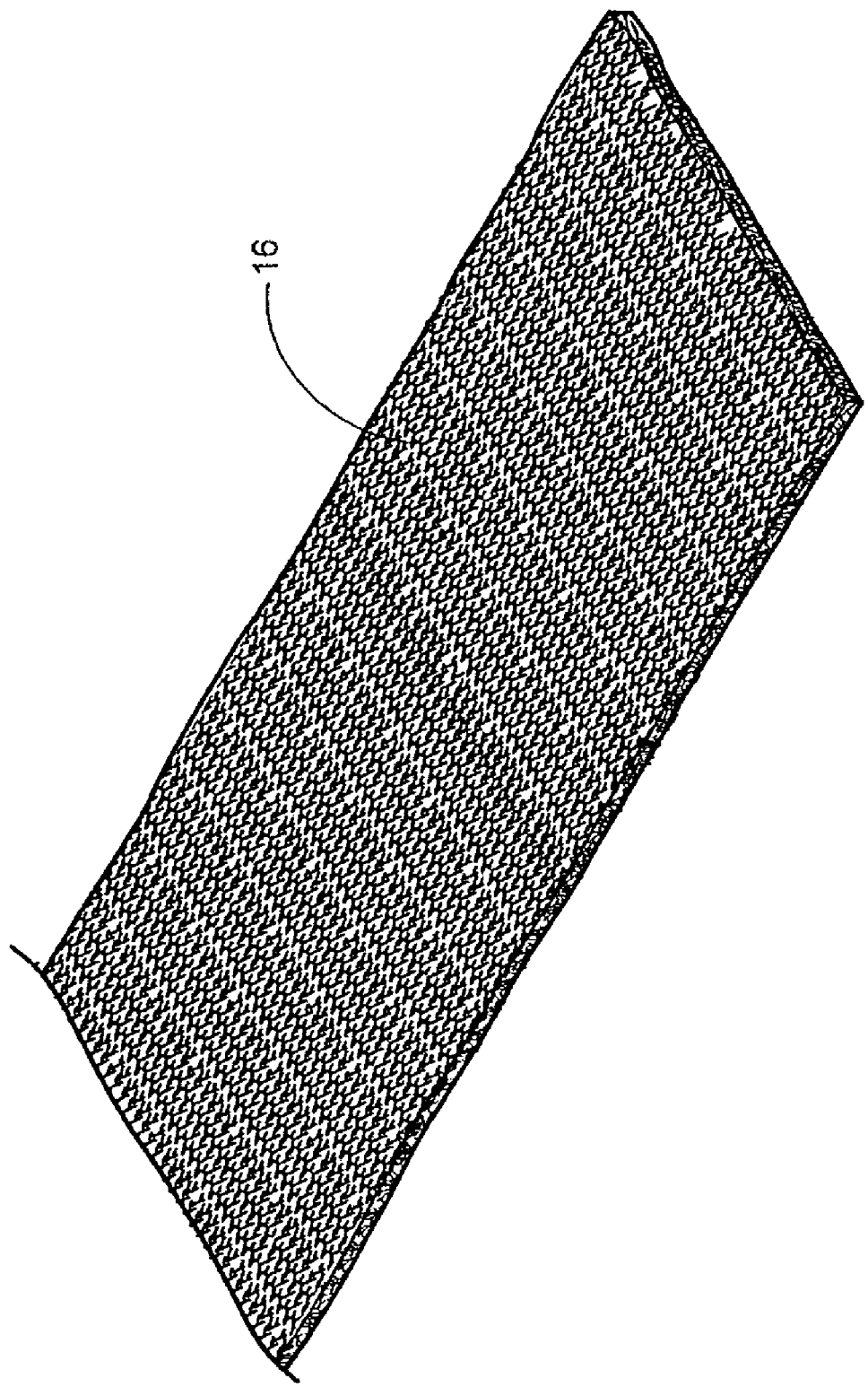
FIG. 7 is a perspective view of a single layer knitted embodiment of the substrate portion of the medical bandage.

A substrate 16 according to one embodiment is shown in FIG. 7, and is impregnated or coated with a reactive system which remains stable when maintained in substantially moisture-free conditions but which hardens upon exposure to sufficient moisture to form a rigid, self-supporting structure. Two typical formulations of the reaction system is set forth in the following tables:

TABLE 1

| Isonate ↓ 143L | or | | |
|---|---|---|---|
| Mondur ↓ CD | or | polyisocyanate | 50.0% |
| Rubinate ↓ XI168 | | | |
| Pluracol ↓ P1010 | | polyol | 46.6% |
| DC-200 Silicone | | defoaming agent | 0.30% |
| Benzoyl Chloride | | stabilizer | 0.10% |
| Thancat. DM-70 | | catalyst | 3.0% |
| | | | 100% |

TABLE 2

| Isonate 143L | or | | |
|---|---|---|---|
| Mondur CD | or | Polyisocyanate | 50.0% |
| Carbowax PEG 600 | | | |
| Carbowax PEG 4600 | | | 22.0% |
| Carbowax PEG 8000 | | | |
| Voranol 230-238 | | | |
| Voranol 220-110 | | | 18.0% |
| Irganox 1010 | | | 2.0% |
| Antifoam 1400 | | | 4.0% |
| Methane Sulphonic Acid | | | 1.0% |
| DMDEE | | | 3.0% |
| | | | 100% |

These formulations and their varying proportions are well-known.

By continued reference to FIG. 7, the substrate 16 according to one embodiment is formed of a single layer of a knitted double fabric impregnated with a resin, for example, one of the moisture-curable resins identified above, but also may utilize a wide range of available polymer chemistries, including but not limited to polyurethanes, polyureas, polyesters, polyacrylates and epoxy. In one of the preferred embodiments, the substrate 16 comprises a warp knitted double fabric impregnated with a moisture curable polyurethane resin. The warp knitted double fabric can be constructed using any suitable organic or inorganic yarns/fibers such as glass, high tenacity polyester, polypropylene, aramid fibers (Kevlar®) and ultra high molecular weight polyethylene (Spectra®). The yarn count ranges are preferably between 20 Tex to 136 Tex and preferably 44 Tex to 136 Tex. The warp knitted double fabric formed a three-dimensional substrate 16 having a top and a bottom layer that are interconnected using plurality of yarns. The yarns used for forming the top layer, bottom layer and the interconnection between them can be constructed from the same or different materials.

In one of the preferred embodiments, the substrate 16 is knitted on a double bed warp knitted machine with six guide bars. The preferred fabric notation is an inlay with a chain stitch on the surface and a "V" or a butterfly stitch in the center. The yarns are knitted into a three-dimensional fabric substrate having sufficient weight and thickness to keep the resin within the substrate. Any otherwise suitable substrate can also be used in combination with the cover 18.

The fabric structure can be tailored for any level of course and wales density. However, in the preferred construction, the fabric that forms the substrate 16 comprises 450-580 courses per meter, with a preferred range of 500-550 courses per meter and 19 wales per 10 cm, with a preferred range of 15-25 wales per 10 cm. The fabric can be constructed into any suitable width for varying limb sizes and shapes. The most preferred knitted fabric widths vary in the range of 2.5 cm to 60 cm. The fabric thickness is an important feature as it effects the final rigidity and is also important aesthetically for patient's comfort and ease of use. The warp knitted fabric in this embodiment can vary in thickness range from 1 mm to 10 mm and preferably in the range of 2 mm to 5 mm. The final fabric weight will depend on various factors such as fabric construction, yarns used and other factors that are well known in the prior art. In the most preferred structure, the fabric weight will vary in the range of 500 to 3000 grams/m$^2$, and even more preferably in the range of 1000 to 1800 grams/m$^2$.

According to one preferred embodiment of the invention, fiberglass yarns are used to construct the single layer fabric of the substrate 16. Fiberglass possesses certain advantages because of its low cost and the experience developed over years of use in conventional fiberglass splints.

Figure 8:
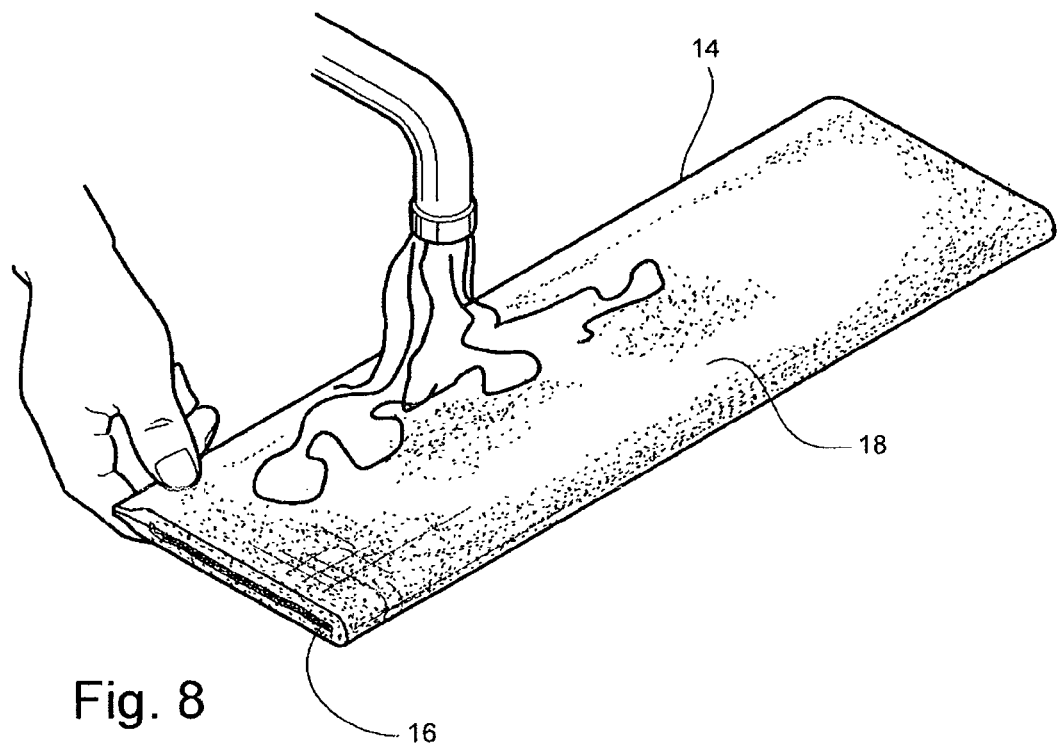
FIG. 8 is a view showing the medical bandage being activated by wetting with water.
Figure 9:
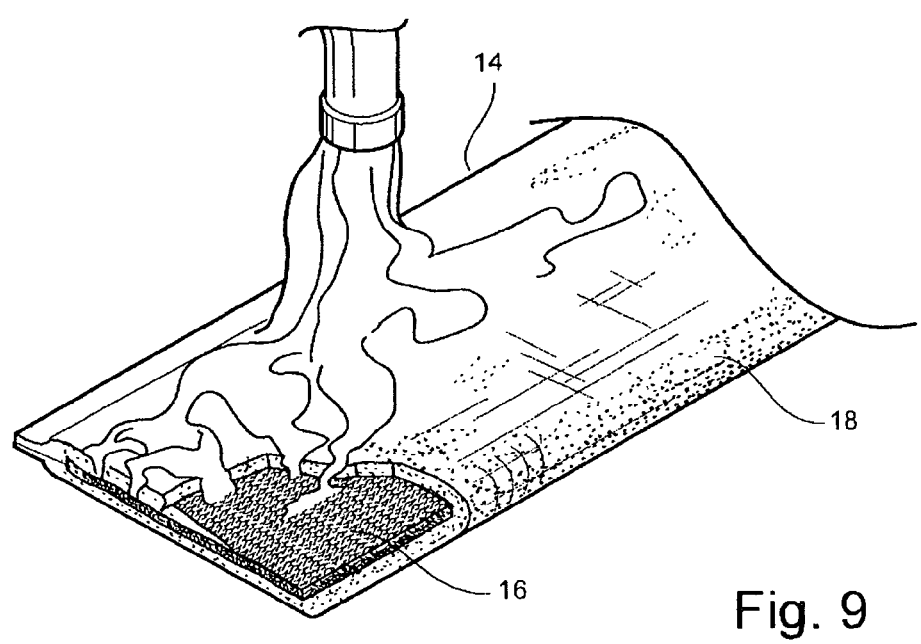
FIG. 9 is a view showing the free flow of water through the cover to the substrate.
Figure 10:
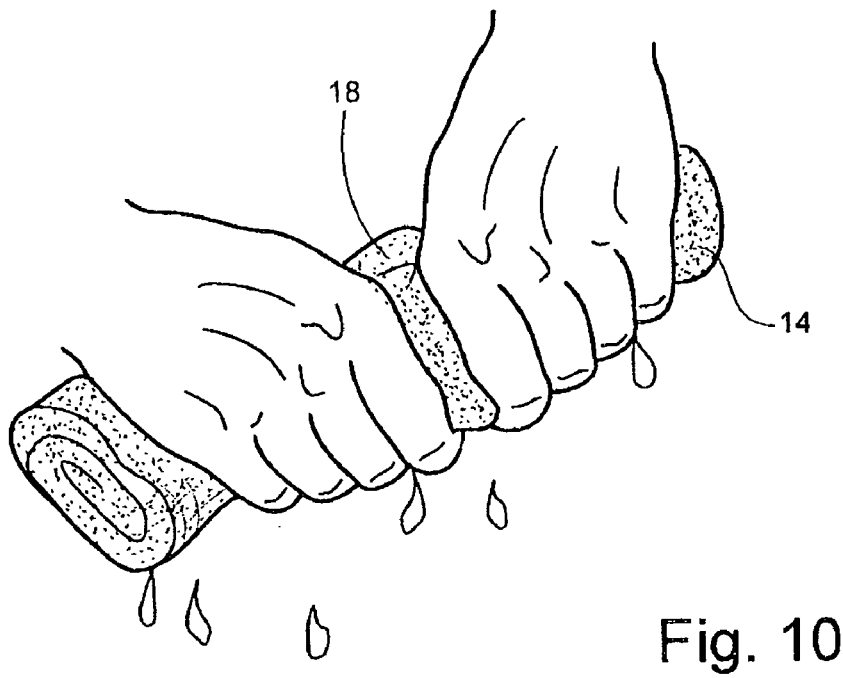
FIG. 10 is a view showing excess water being removed from the medical bandage before application.
Figure 11:
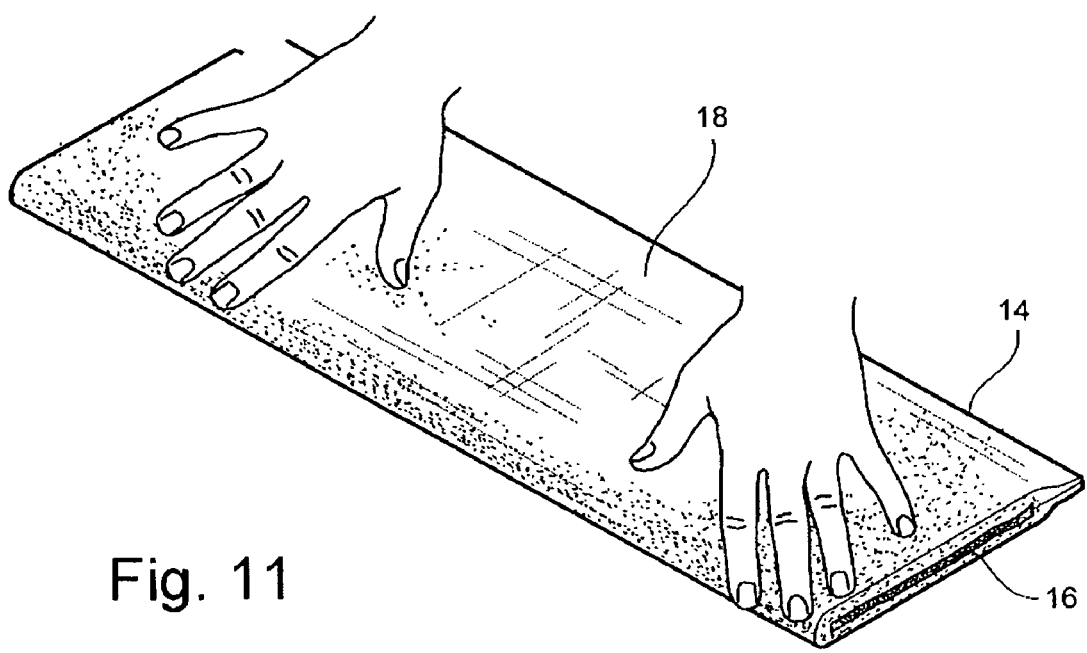
FIG. 11 is a view showing the medical bandage being smoothed and straightened before application to a patient.

Referring now to FIGS. 8-11, the bandage 14 is typically activated by spraying or pouring water on one surface of the bandage 14, FIGS. 8 and 9, wringing out the excess water, FIG. 10, and smoothing the bandage before application, FIG. 10. The cover 18 exhibits excellent cohesion while being smoothed for application, with minimal tendency to wrinkle.

Figure 12:
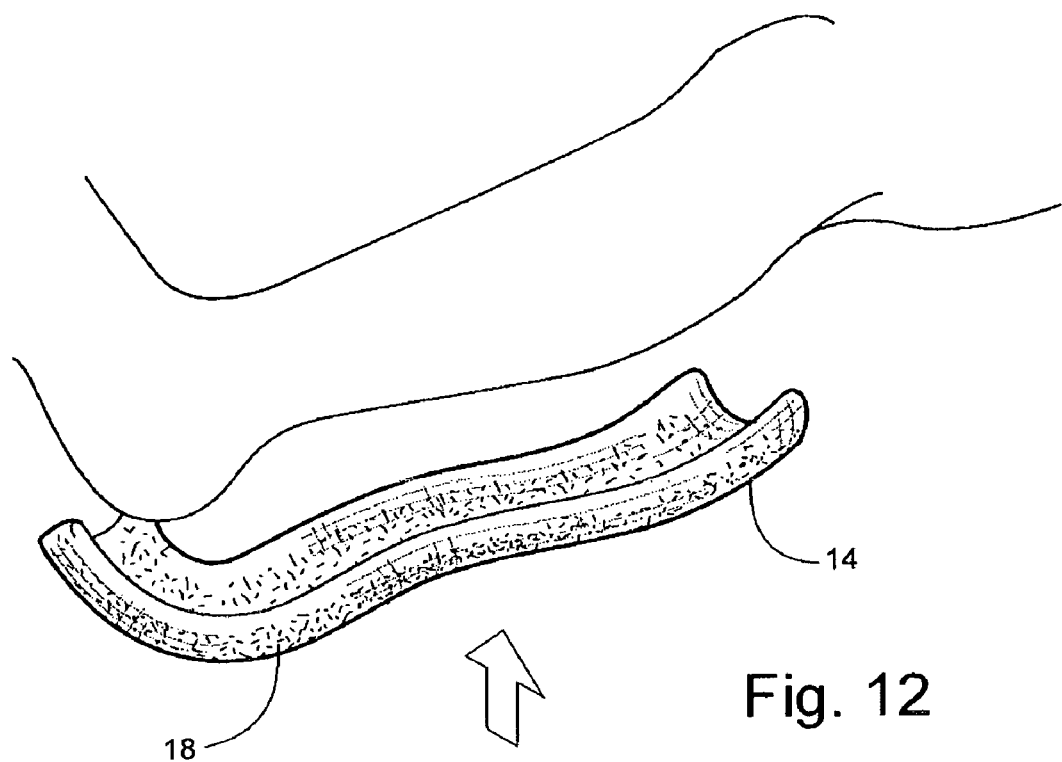
FIGS. 12 and 13 are perspective views of the medical bandage being placed on an injured limb and being secured into place by a covering wrap.

As is shown in FIG. 12, an appropriate length of material 14 is formed to the shape of the body member to be immobilized. This particular type of splint, known as a posterior short leg splint, is formed by molding a length of the product 14 to the calf and up over the heel and onto the foot. Then, product 14 is overwrapped with an elastic conventional bandage "B", as is shown in FIG. 10.

Figure 14:
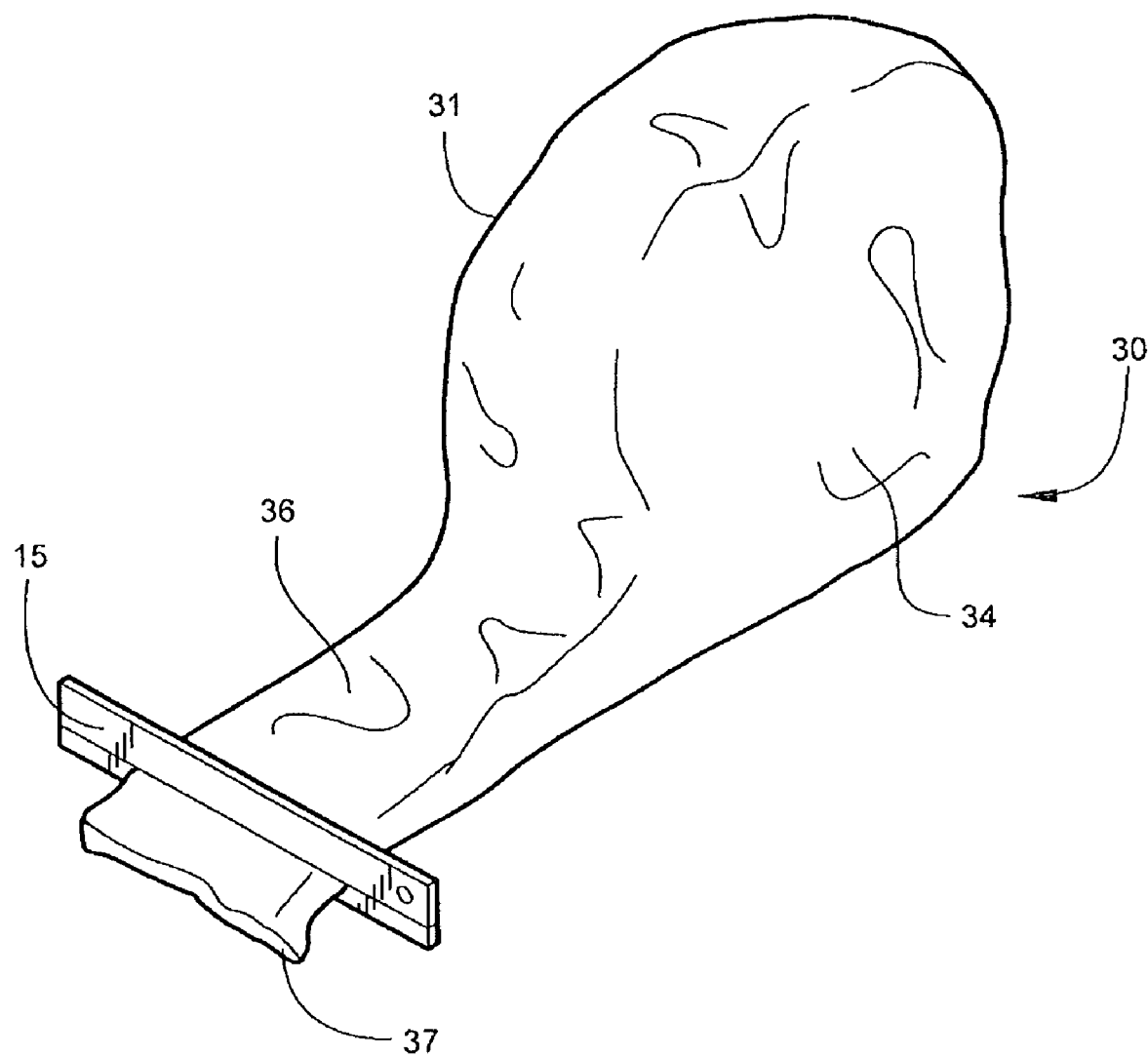
FIG. 14 is a perspective view of an alternative design of a dispensing container for holding the medical bandage until ready for dispensing.
Figure 15:
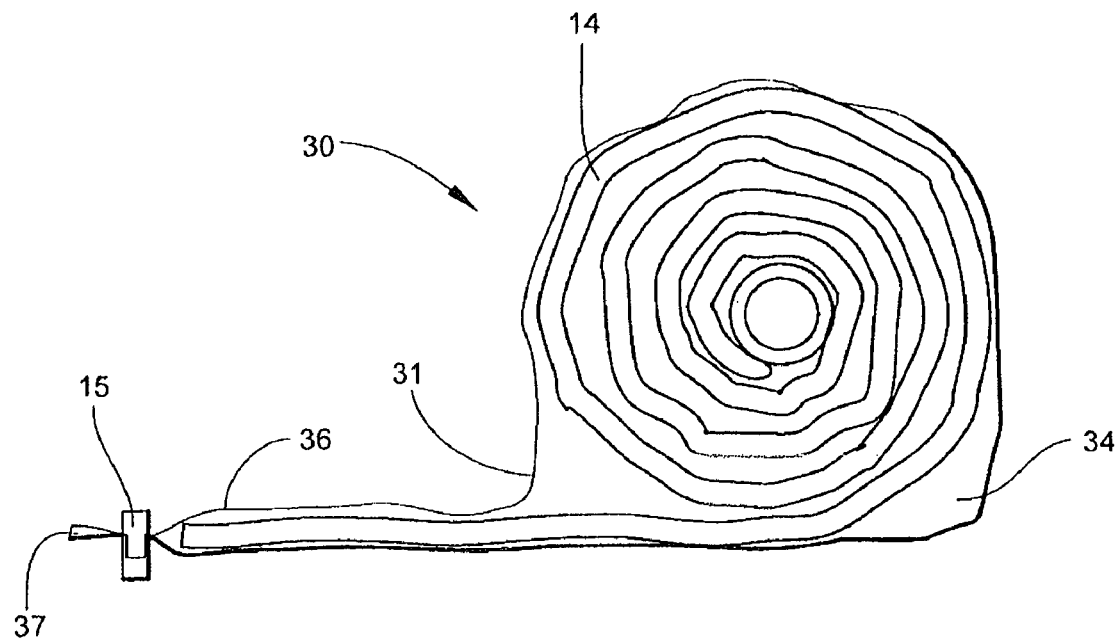
FIG. 15 is a vertical cross-section of the dispensing container shown in FIG. 11.
Figure 16:
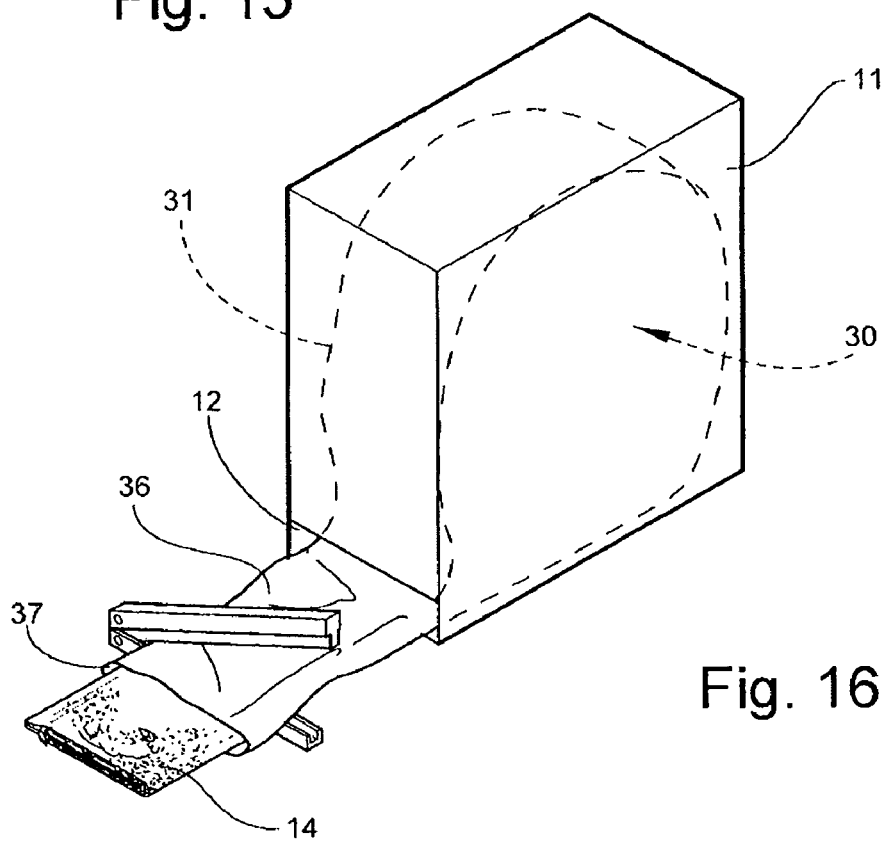
FIG. 16 is a perspective view of the dispenser carton into which the container may optionally be positioned.

Referring now to FIGS. 14-16, a medical bandaging product according to another embodiment of the invention is shown at broad reference numeral 30. The medical bandage 14 is positioned within a container 31 which is formed of two laminated elongate sheets placed in registration and heat sealed along a common seam to form a moisture proof container of the same material and construction as the sleeve 13. The outer layer is a tear-resistant plastic film and the middle layer is aluminum foil that acts as a moisture barrier. The inner layer is a plastic film having thermoplastic properties suitable for heat sealing the interior of container 31 securely against moisture.

As is also shown in FIG. 14, container 31 includes an enlarged product storage package 34 in which is contained a coil of the medical bandage 14. Package 34 is integral and communicates with an elongate dispensing sleeve 36 having an openable end 37 through which the medical bandage 14 in the container 31 is dispensed.

As is shown in FIGS. 15 and 16, the end 37 of dispensing sleeve 32 may be sealed with a clamp of any suitable type, such as a bar clamp 15, or any other suitable closure. The dispensing sleeve 36 fits snugly around the medical material 14 in order to limit exposure of the medical material 14 to air which enters when the opening 37 is unsealed for dispensing the medical bandage 14. FIG. 15 also shows that the medical material 14 is coiled into a relatively tight coil to limit exposure to air and sealed into the container 31. When opening 37 is properly sealed, container 31 is sufficiently airtight so that medical material 14 remains in its soft, uncured state for much longer that the usual length of time needed to exhaust the supply of medical material 14 in container 31. If a short length of the medical material 14 adjacent the opening 37 hardens, it can be cut away and discarded.

A desired length of medical material 14 is dispensed by removing clamp 15 and grasping the exposed end of the medical material 14. The appropriate length is pulled out of container 31—the medical material 14 uncoiling in the storage package 34. When the proper length has been dispensed through opening 37, it is cut and the end is tucked back into the dispensing sleeve 36. The open end 37 is quickly resealed.

Figure 13:
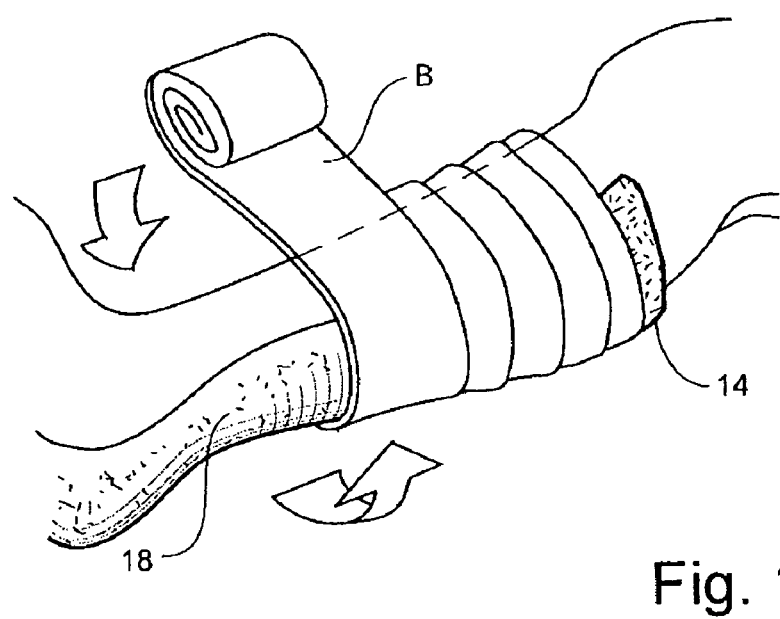

As is shown in FIG. 13, if desired, the medical bandaging product 30 can be placed inside a dispensing carton 11, with the dispensing sleeve 36 of container 31 projecting out of the slot 12 in the bottom of carton 11.

Figure 17:
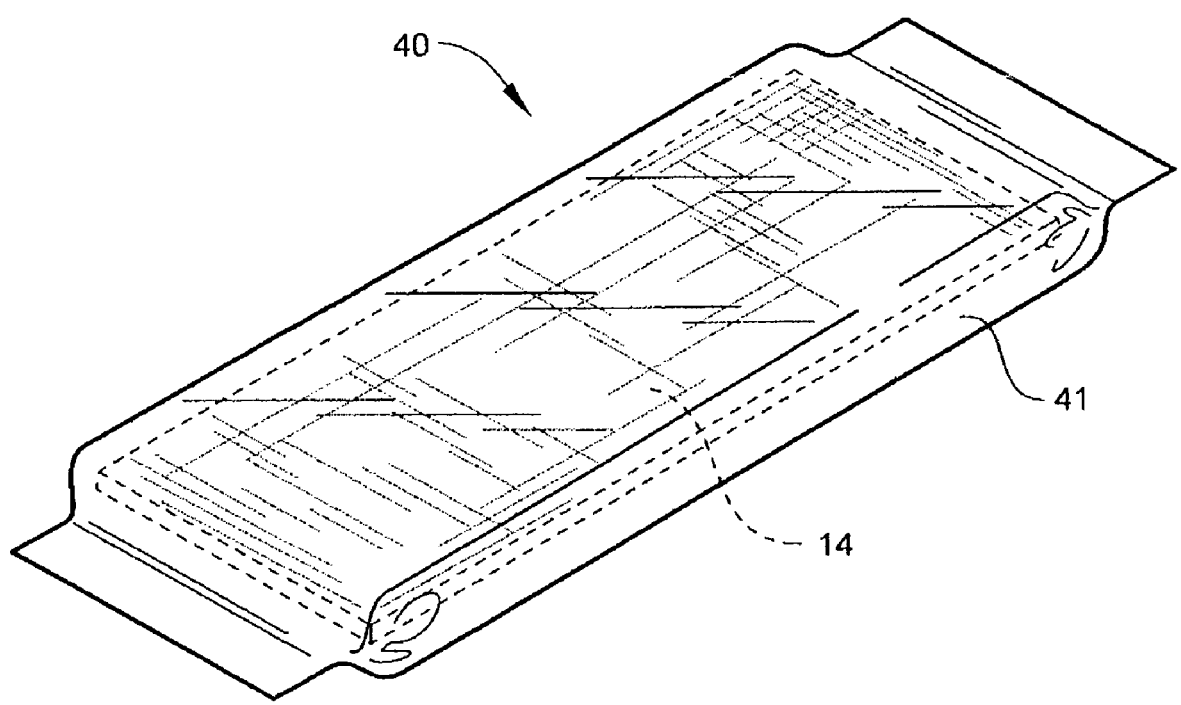
FIG. 17 is a perspective view of a pre-cut medical bandage stored for use in a moisture-impervious envelope until ready for use.
Figure 18:
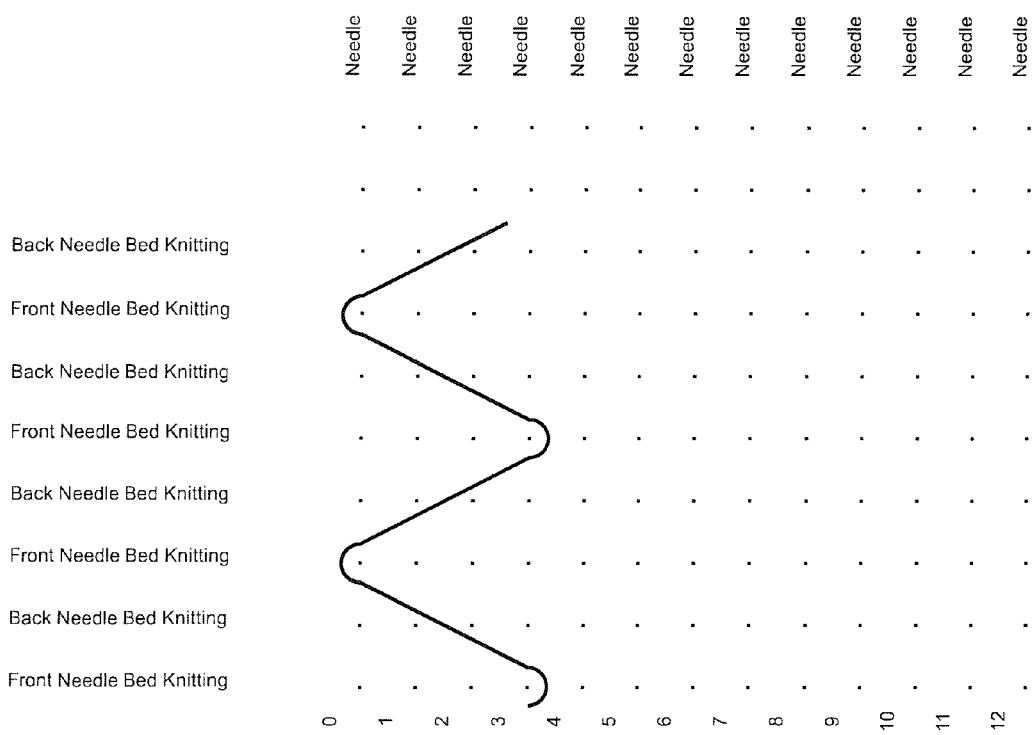
Figure 19:
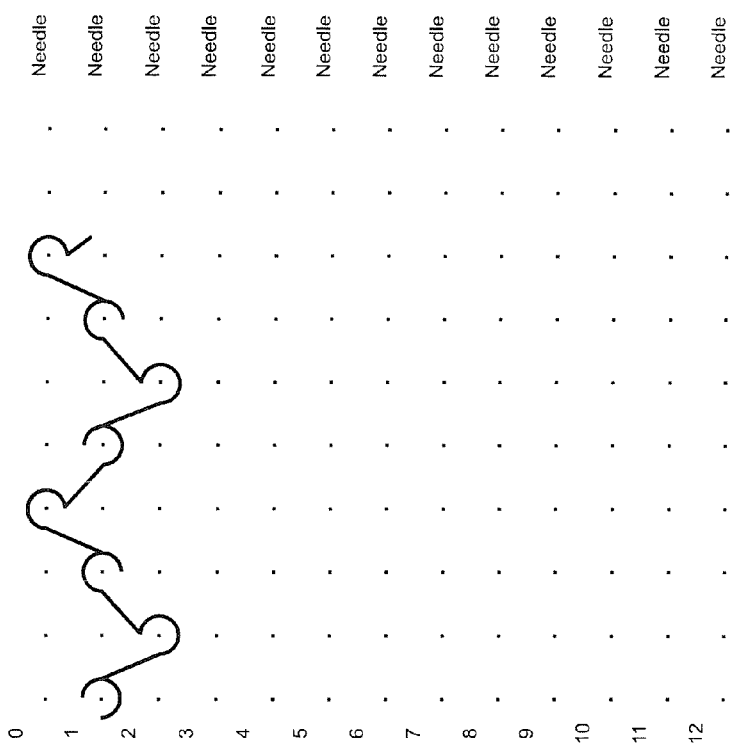
Figure 21:
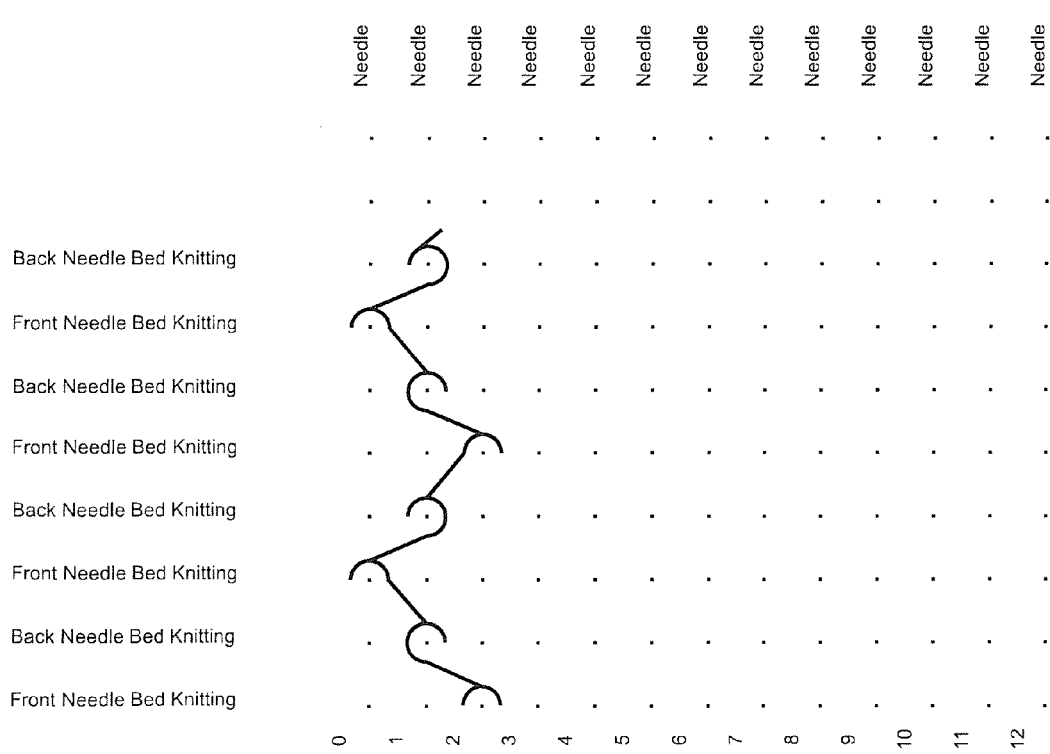
Figure 22:
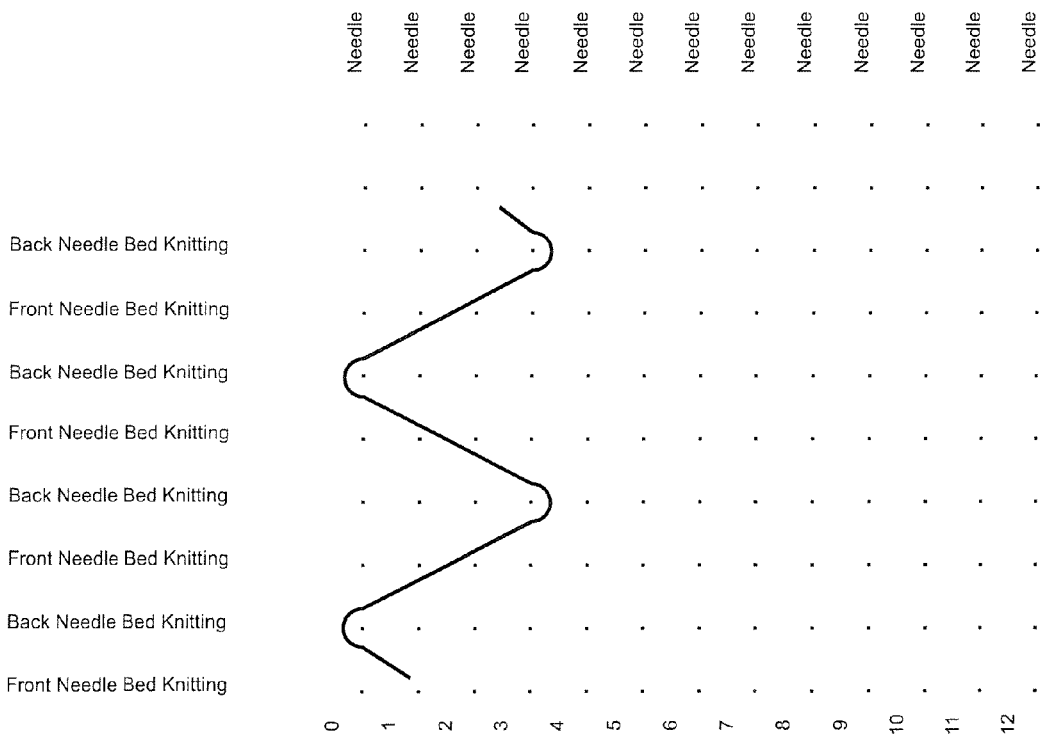

Referring now to FIG. 17, a pre-cut embodiment of a medical bandage product 40 is shown. The medical bandage product 40 comprises a moisture-impervious envelope 41 in which is packaged a pre-cut length of the medical bandage 14, preferably having the structure and characteristics described above with reference to FIGS. 1-16. The medical bandaging product 40 is sized according to the desired end use and is labeled as such. The medical bandage 14 may be removed from the envelope 41 and used as is, or cut and shaped as needed to meet the medical requirements of the treating physician and technician.

A cover for a medical bandage, a medical bandage, a medical bandaging product and related methods are described above. Various details of the invention may be changed without departing from its scope. Furthermore, the foregoing description of the preferred embodiment of the invention and the best mode of practicing the invention are provided for the purpose of illustration only and not for the purpose of limitation—the invention being defined by the claims.

I claim:

1. A cover fabric for a medical bandage, comprising: a knitted spacer fabric containing a moisture-hardenable substrate, the knitted spacer fabric comprising monofilament yarn having a diameter from about 0.07-1.14 mm and multifilament yarn including from about 24-48 filaments, the spacer fabric having a weight from about 90-200grams/m$^2$ and an uncompressed thickness of about 2.5 mm to characterize the cover as padding, the spacer fabric further having a moisture vapor transmission rate range from about 900-1050g/24 hrs/m$^2$ and an air permeability range from about 3200-4500cm$^3$/cc$^2$ per hour at 20 cm Mercury, wherein the knitted spacer fabric has a stitch pattern according to:

| | | |
|---|---|---|
| Bar1. 16-16/8-8/0-0/8-8 | Inlay over 4 needles | 18 gauge |
| Bar2. 0-4/4-4/4-0/0-0 | Chain Stitch | 18 gauge |
| Bar3. 4-8/12-8/4-8/4-0 | 3 Needle 'V' | 9 gauge |
| Bar4. 0-4/12-8/16-20/12-8 | 5 Needle 'V' | 9 gauge |
| Bar5. 4-4/4-0/0-0/0-4 | Chain stitch | 9 gauge |
| Bar6. 0-0/12-12/24-24/24-24/24/24/12-12/0-0/0-0/0-0 | Inlay over 3 needles | 9 gauge. |

2. A cover fabric according to claim 1, wherein the knitted spacer fabric comprises monofilament and multifilament yarns.

3. A cover fabric according to claim 1, wherein the knitted spacer fabric includes monofilament yarns that are selected from the group consisting of polyester, polypropylene, polyethylene or nylon, and multifilament yarns that are selected from the group consisting polyester, polypropylene or nylon.

4. A cover fabric according to claim 1, wherein all bars are fully threaded.

5. A medical bandage, comprising:
(a) a protective, knitted spacer fabric cover positioned in surrounding relation on a moisture-hardenable substrate, the knitted spacer fabric comprising monofilament yarn having a diameter from about 0.07-1.14 mm and multifilament yarn including from about 24-48 filaments, the spacer fabric having a weight from about 90-200 grams/m$^2$ and an uncompressed thickness of about 2.5 mm to characterize the cover as padding, the spacer fabric further having a moisture vapor transmission rate range from about 900-1050 g/24 hrs/m$^2$ and an air permeability range from about 3200-4500 $cm^3/cc^2$ per hour at 20 cm Mercury;

(b) the substrate being comprised of an elongate fabric having two opposed major faces connected by yarns extending between the faces, and two opposed, longitudinally-extending side edges defining a predetermined fabric thickness; and (c) a reactive system applied to and into the thickness of the substrate, the reactive system having a first state wherein the substrate remains in a flexible, conformable condition and a second state wherein the reactive system hardens, simultaneously hardening the substrate into a desired conformation, wherein the knitted spacer fabric has a stitch pattern according to:

| Bar1. | 16-16/8-8/0-0/8-8 | Inlay over 4 needles | 18 gauge |
|---|---|---|---|
| Bar2. | 0-4/4-4/4-0/0-0 | Chain Stitch | 18 gauge |
| Bar3. | 4-8/12-8/4-8/4-0 | 3 Needle 'V' | 9 gauge |
| Bar4. | 0-4/12-8/16-20/12-8 | 5 Needle 'V' | 9 gauge |
| Bar5. | 4-4/4-0/0-0/0-4 | Chain stitch | 9 gauge |
| Bar6. | 0-0/12-12/24-24/24-24/24/24/12-12/0-0/0-0/0-0 | Inlay over 3 needles | 9 gauge. |

6. A medical bandage according to claim 5, wherein the reactive system comprises a moisture-curable resin.

7. A medical bandage according to claim 5, wherein the cover comprises a soft, flexible protective padding covering at least one of the major faces of the substrate and adapted to pass water therethrough and onto the substrate.

8. A medical bandage according to claim 5, wherein the bandage is packaged in a moisture-proof condition in a precut length.

9. A medical bandage according to claim 5, wherein the bandage is in the form of a roll from which desired lengths may be cut as needed.

10. A medical bandaging product, comprising:
(a) a sleeve formed of moisture-5 material and sealable to prevent entry of moisture;
(b) a medical material positioned in the sleeve and sealed therein against entry of moisture until use, the medical material comprising a substrate formed of an elongate fabric having two opposed major faces and two opposed, longitudinally-extending side edges defining a predetermined fabric thickness;
(c) a reactive system impregnated into or coated onto the substrate, the system remaining stable when maintained in substantially moisture-free conditions and hardening upon exposure to sufficient moisture to form a rigid, self supporting structure; and
(d) a soft, flexible, protective knitted spacer fabric cover positioned over at least one of the major faces of the substrate along its length to provide a barrier between the substrate and the skin of a patient when the material is in use, the knitted spacer fabric comprising monofilament yarn having a diameter from about 0.07-1.14 mm and multifilament yarn including from about 24-48 filaments, the spacer fabric having a weight from about 90-200 grams/$m^2$ and an uncompressed thickness of about 2.5 mm to characterize the cover as padding, the spacer fabric further having a moisture vapor transmission rate range from about 900-1050 g/24 hrs/$m^2$ and an air permeability range from about 3200-4500 $cm^3/cc^2$ per hour at 20 cm Mercury, wherein the knitted spacer fabric has a stitch pattern according to:

| Bar1. | 16-16/8-8/0-0/8-8 | Inlay over 4 needles | 18 gauge |
|---|---|---|---|
| Bar2. | 0-4/4-4/4-0/0-0 | Chain Stitch | 18 gauge |
| Bar3. | 4-8/12-8/4-8/4-0 | 3 Needle 'V' | 9 gauge |
| Bar4. | 0-4/12-8/16-20/12-8 | 5 Needle 'V' | 9 gauge |
| Bar5. | 4-4/4-0/0-0/0-4 | Chain stitch | 9 gauge |
| Bar6. | 0-0/12-12/24-24/24-24/24/24/12-12/0-0/0-0/0-0 | Inlay over 3 needles | 9 gauge. |

11. A medical bandaging product according to claim 10, wherein the cover is positioned over both major faces of the substrate.

12. A medical bandaging product according to claim 10, wherein the cover is wrapped around and encloses both major faces and the longitudinally extending side edges of the substrate.

* * * * *

UNITED STATES PATENT AND TRADEMARK OFFICE
CERTIFICATE OF CORRECTION

| | | |
|---|---|---|
| PATENT NO. | : 7,960,603 B2 | Page 1 of 1 |
| APPLICATION NO. | : 12/019672 | |
| DATED | : June 14, 2011 | |
| INVENTOR(S) | : John C. Evans | |

It is certified that error appears in the above-identified patent and that said Letters Patent is hereby corrected as shown below:

Column 11, line 39, "moisture-5" should read "moisture-impervious".

Signed and Sealed this
Thirty-first Day of January, 2012

David J. Kappos
*Director of the United States Patent and Trademark Office*